US 8,486,011 B2

(12) United States Patent
O'Dea et al.

(10) Patent No.: US 8,486,011 B2
(45) Date of Patent: Jul. 16, 2013

(54) SYSTEM AND A METHOD FOR INFLATING AN INFLATABLE ELEMENT WITH A LIQUID INFLATING MEDIUM AND A BALLOON CATHETER INFLATED BY THE SYSTEM AND METHOD (75) Inventors: John O'Dea, Bearna (IE); Eoin Bambury, Navan (IE)

(73) Assignee: Flip Technologies Limited, Dangan (IE)

( * ) Notice: Subject to any disclaimer, the term of this patent is extended or adjusted under 35 U.S.C. 154(b) by 94 days.

(21) Appl. No.: 12/937,082

(22) PCT Filed: Apr. 9, 2009

(86) PCT No.: PCT/IE2009/000014
§ 371 (c)(1),
(2), (4) Date: Nov. 16, 2010

(87) PCT Pub. No.: WO2009/125380
PCT Pub. Date: Oct. 15, 2009

(65) Prior Publication Data
US 2011/0054395 A1    Mar. 3, 2011

(30) Foreign Application Priority Data

Apr. 9, 2008 (IE) .................................. S2008/0265

(51) Int. Cl.
*A61M 29/00* (2006.01)
(52) U.S. Cl.
USPC .................. 604/99.03; 604/99.01; 604/97.01

(58) Field of Classification Search
USPC ...................... 604/97.01–97.03, 99.01–99.03
See application file for complete search history.

(56) References Cited

U.S. PATENT DOCUMENTS

| 4,740,203 | A | * | 4/1988 | Hoskins et al. ............... 604/191 |
| 4,793,351 | A |   | 12/1988 | Landman et al. |
| 4,955,905 | A | * | 9/1990 | Reed .................................. 623/8 |
| 5,190,046 | A | * | 3/1993 | Shturman ...................... 600/463 |
| 5,209,731 | A | * | 5/1993 | Sterman et al. ............. 604/97.02 |
| 5,254,092 | A | * | 10/1993 | Polyak ....................... 604/99.02 |
| 5,372,584 | A | * | 12/1994 | Zink et al. ..................... 604/515 |
| 5,458,571 | A | * | 10/1995 | Lampropoulos et al. ..... 604/509 |
| 5,527,280 | A | * | 6/1996 | Goelz ........................ 604/99.02 |

(Continued)

FOREIGN PATENT DOCUMENTS

| EP | 0184314 A1 | 6/1986 |
| EP | 1199083 A1 | 4/2002 |

(Continued)

*Primary Examiner* — Victoria P Shumate
(74) *Attorney, Agent, or Firm* — Sughrue Mion, PLLC (57) ABSTRACT

A balloon of a balloon catheter is inflated with a liquid inflating medium by a syringe through a flow line. Air in the flow line and the balloon is displaced into a return line. The balloon is deflated by drawing the liquid inflating medium from the balloon along with the air in the return line into the syringe where the air is trapped in the syringe. The balloon is reinflated and deflated by the syringe until the level of air in the liquid inflating medium has been reduced to a predefined level. A first non-return valve and a second non-return valve are provided in the flow and return lines, so that the liquid inflating medium is prevented from flowing from the balloon to the syringe in the flow line and from the syringe to the balloon in the return line.

21 Claims, 5 Drawing Sheets

U.S. PATENT DOCUMENTS

| | | | |
|---|---|---|---|
| 5,685,848 A * | 11/1997 | Robinson et al. | 604/97.03 |
| 6,110,143 A * | 8/2000 | Kamen | 604/97.02 |
| 6,176,843 B1 * | 1/2001 | DiCaprio et al. | 604/99.03 |
| 7,169,161 B2 * | 1/2007 | Bonnette et al. | 606/191 |
| 7,220,243 B2 * | 5/2007 | Bonnette et al. | 604/99.01 |
| 2005/0261626 A1 * | 11/2005 | Arai et al. | 604/96.01 |
| 2007/0142818 A1 * | 6/2007 | Webler et al. | 604/509 |

FOREIGN PATENT DOCUMENTS

| | | |
|---|---|---|
| EP | 2014330 A2 | 1/2009 |
| WO | 89/02763 A1 | 4/1989 |
| WO | 2004/075928 A2 | 9/2004 |
| WO | 2007/036035 A1 | 4/2007 |

* cited by examiner

SYSTEM AND A METHOD FOR INFLATING AN INFLATABLE ELEMENT WITH A LIQUID INFLATING MEDIUM AND A BALLOON CATHETER INFLATED BY THE SYSTEM AND METHOD

FIELD OF THE INVENTION

The present invention relates to a system and a method for inflating an inflatable element with a liquid inflating medium, and in particular, though not limited to such a system and method for inflating a balloon of a balloon catheter. The invention also relates to a balloon catheter and to a method and apparatus for determining one of the volume and the cross-sectional area of one of a lumen and a vessel.

BACKGROUND OF THE INVENTION

Balloon catheters are commonly used for carrying out a procedure or an investigation at a remote location in a human or animal subject. For example, such balloon catheters are used for determining the volume of a stomach, or a part thereof subsequent to bariatric surgery. Such balloon catheters are also used for determining the transverse cross-sectional area at locations within the stomach, or of a sphincter, for example, an oesophageal sphincter. Additionally, such balloon catheters are used for determining the transverse cross-sectional area of a vessel or lumen, for example, the oesophagus, and in particular, a diseased portion of the oesophagus which may have resulted in an occlusion. Additionally, such balloon catheters are used for dilating an occlusion in a vessel or lumen, for example, for dilating an occlusion in the oesophagus resulting from a diseased portion of the oesophagus. Such balloon catheters are also used for ablating diseased tissue in a lumen or vessel, such as the oesophagus. Such balloon catheters are also used for determining the volume and/or transverse cross-sectional area of vessels and lumens.

Similarly, such balloon catheters are used for carrying out procedures and investigations in the cardiovascular system, for example, for determining the volume and/or transverse cross-sectional area of a vessel of the cardiovascular system, and are also used for dilating an occlusion in a vessel of the cardiovascular system, as well as for stent placement and ablating tissue in a vessel of the cardiovascular system.

Such balloon catheters comprise an elongated catheter extending between a proximal end and a distal end, and an inflatable element, namely, a balloon located on the catheter, which typically, is located towards the distal end of the catheter. The catheter extends through the balloon so that the balloon defines with the catheter an annular hollow interior region. Typically, a lumen extends through the catheter from the proximal end thereof to the balloon which communicates with the hollow interior region of the balloon for inflating the balloon. Inflating and deflating of the balloon is carried out by delivering and withdrawing, typically, a liquid inflating medium into the balloon through the inflating lumen. In order to facilitate determining the volume or the transverse cross-sectional area of a vessel or lumen within which the balloon is located, at least one, and typically a pair of stimulating electrodes are provided within the balloon on the catheter axially spaced apart from each other, and a plurality of axially spaced apart sensing electrodes are provided within the balloon on the catheter between and axially spaced apart from the stimulating electrodes. A plurality of mutually insulating wires extend through a wire accommodating lumen which extends from the proximal end to the balloon so that the wires can be individually coupled to corresponding ones of the stimulating and sensing electrodes. When the balloon is inflated with an electrically conductive inflating medium, which typically is a liquid saline solution, by applying a stimulating electrical current of known constant value to the stimulating electrodes, voltages produced on the sensing electrodes are indicative of the transverse cross-sectional area of the balloon adjacent the respective sensing electrodes. Accordingly, by reading the voltages produced on the sensing electrodes, the transverse cross-sectional area of the balloon adjacent the sensing electrodes can be computed, and in turn the volume of the balloon can be computed. Thus, by inflating the balloon to fill the vessel or lumen, the volume and the transverse cross-sectional area of the vessel or lumen at locations adjacent the sensing electrodes can be computed by reading the voltages produced on the sensing electrodes resulting from the constant current signal applied to the stimulating electrodes.

Such balloon catheters will be known to those skilled in the art.

However, a problem with such balloon catheters is that it is difficult to determine when precisely the balloon has been inflated so that the balloon just fills the vessel or lumen the volume or the transverse cross-sectional area of which is to be determined without dilating the vessel or lumen. In general, in order to determine when the balloon has been inflated to just fill the vessel or lumen, the pressure of the inflating medium is monitored. This, typically, requires the provision of a pressure sensor at the proximal end of the catheter of the balloon catheter, which monitors the pressure of the inflating medium adjacent the proximal end of the catheter. Inflating of balloon catheters is normally carried out by pumping the inflating medium, which, in general, is a liquid, such as an electrically conductive saline solution, into the balloon through the inflating lumen from a syringe containing the inflating medium. Alternatively, the inflating medium may be pumped from a reservoir by a suitable pump. Prior to inflating the balloon, both the balloon and the inflating lumen contain air. Thus, where the inflating medium is a liquid inflating medium, after inflating of the balloon with the liquid inflating medium, the inflating medium in the balloon and in the inflating lumen of the balloon catheter will include air. The presence of air in the liquid inflating medium in both the balloon and in particular, in the inflating lumen of the balloon catheter renders it virtually impossible to obtain a true pressure reading of the pressure of the liquid inflating medium in the balloon. The air in the liquid inflating medium forms an air pocket in the inflating lumen, which results effectively in an open hydraulic circuit between the balloon and the proximal end of the catheter. Accordingly, the presence of such an air pocket in the inflating lumen acts to prevent the pressure sensor at the proximal end of the catheter producing a true reading of the pressure of the liquid inflating medium in the balloon.

SUMMARY OF THE INVENTION

There is therefore a need for a method and a system for inflating a balloon of a balloon catheter and for inflating any type of inflatable element of a balloon catheter which addresses this problem.

The invention is directed towards a method and a system for inflating an inflatable element with a liquid inflating medium, and the invention is also directed towards a balloon catheter and a method for inflating the balloon of a balloon catheter. The invention is also directed towards a method and apparatus for determining one of a volume and the transverse cross-sectional area of one of a lumen and a vessel.

According to the invention there is provided a system for inflating an inflatable element with a liquid inflating medium, the system comprising a separating means for separating the liquid inflating medium from a gaseous medium therein, a flow line communicating the inflatable element with the separating means, a return line communicating the inflatable element with the separating means, and a pump means selectively and alternately operable to deliver the liquid inflating medium from the separating means to the inflatable element for inflating thereof, and to deliver the liquid inflating medium from the inflatable element to the separating means for separating the liquid inflating medium from the gaseous medium therein, so that after initial inflating of the inflatable element with the liquid inflating medium through the flow line, the inflatable element is deflated by delivering the liquid inflating medium from the inflatable element through the return line to the separating means, and the inflatable element is re-inflated with the liquid inflating medium through the flow line from the separating means with the gaseous medium separated therefrom.

In one aspect of the invention the pump means is operable for sequentially delivering the liquid inflating medium from the inflatable element to the separating means through the return line, and from the separating means to the inflatable element through the flow line until the level of gaseous medium in the liquid inflating medium has been reduced to a desired level.

In another aspect of the invention the pump means is operable for sequentially delivering the liquid inflating medium from the inflatable element to the separating means through the return line and from the separating means to the inflatable element through the flow line until the level of gaseous medium in the liquid inflating medium has been reduced to a level which permits a true reading of the pressure of the liquid inflating medium in the inflatable element to be obtained from a reading of the pressure of the liquid inflating medium in one of the flow line and the return line.

In one embodiment of the invention a valving means for selectively and alternately coupling the separating means to the flow line and the return line is provided.

In another embodiment of the invention the pump means is located intermediate the valving means and the separating means.

Preferably, the valving means comprises a first non-return valve located in the return line communicating the return line with the separating means, the first non-return valve being configured for permitting flow of the liquid inflating medium through the return line from the inflatable element to the separating means.

Advantageously, the valving means comprises a second non-return valve located in the flow line communicating the flow line with the separating means, the second non-return valve being configured for permitting flow of the liquid inflating medium through the flow line from the separating means to the inflatable element.

In one embodiment of the invention a main line couples the valving means to the separating means. Advantageously, the pump means is located in the main line.

In another aspect of the invention a pressure sensing means is provided for remotely monitoring the pressure of the liquid inflating medium in the inflatable element. Preferably, the pressure sensing means is located in one of the flow line and the return line for monitoring the pressure of the liquid inflating medium in the inflatable element. Advantageously, the pressure sensing means comprises a first pressure sensing means located in the return line intermediate the separating means and the inflatable element.

In one embodiment of the invention the first pressure sensing means is located adjacent the valving means.

In another embodiment of the invention the first pressure sensing means comprises a first main pressure sensing means for monitoring the pressure of the liquid inflating medium in the inflatable element during inflating thereof.

In a further embodiment of the invention the first pressure sensing means comprises a first secondary pressure sensing means for monitoring the pressure at which the liquid inflating medium is being withdrawn by the pump means from the inflatable element.

In another embodiment of the invention the pressure sensing means comprises a second pressure sensing means located in the flow line intermediate the separating means and the inflatable element. Advantageously, the second pressure sensing means is located adjacent the valving means.

In another embodiment of the invention the second pressure sensing means comprises a second main pressure sensing means for monitoring the pressure of the liquid inflating medium in the inflatable element during deflating thereof.

In a further embodiment of the invention the second pressure sensing means comprises a second secondary pressure sensing means for monitoring the pressure of the liquid inflating medium being delivered by the pump means for inflating the inflatable element.

In one aspect of the invention the separating means comprises a reservoir for the liquid inflating medium, the reservoir being configured so that gaseous medium in the liquid inflating medium rises to a top surface of the liquid inflating medium in the reservoir for separating the liquid inflating medium from the gaseous medium. Preferably, the reservoir comprises an elongated barrel of a syringe, the barrel having a communicating port for communicating the barrel with the flow and return lines. Advantageously, the pump means comprises a piston slideable axially within the barrel of the syringe in a first direction for drawing the liquid inflating medium into the barrel, and in an opposite second direction for discharging the liquid inflating medium from the barrel.

In one aspect of the invention the syringe is configured so that the top surface of the liquid inflating medium in the syringe barrel is above the level of the communicating port in order that the liquid inflating medium separated from the gaseous medium is dischargeable from the syringe barrel through the communicating port without the gaseous medium. Preferably, the syringe barrel is configured so that the communicating port of the syringe barrel is located at a lower portion of the syringe barrel.

In one embodiment of the invention the syringe is configured so that the gaseous medium in the liquid inflating medium rises through the liquid inflating medium in the barrel to a liquid inflating medium/piston interface so that the gaseous medium is trapped between the piston and the liquid inflating medium. Preferably, the syringe is configured so that the piston is operated in the first direction in a generally upward direction, and in the second direction in a generally downward direction.

In an alternative embodiment of the invention the syringe is configured so that the piston is operable in the first direction and the second direction along a substantially horizontal axis.

In another embodiment of the invention the inflatable element is located on an elongated catheter extending between a proximal end and a distal end, a flow lumen and a return lumen extending from the proximal end of the catheter to the inflatable element and communicating with the inflatable element, the flow lumen forming a part of the flow line, and the return lumen forming a part of the return line. Preferably, the flow and return lines are releasably coupleable to the flow and return lumens.

The invention also provides a balloon catheter comprising an elongated catheter extending between a proximal end and a distal end, and an inflatable element located on the catheter, a flow lumen extending from the proximal end of the catheter to the inflatable element and communicating with the inflatable element, a return lumen extending from the proximal end of the catheter to the inflatable element and communicating with the inflatable element, and a system according to the invention with the flow line of the system coupled to the flow lumen of the catheter adjacent the proximal end thereof, and the return line of the system coupled to the return lumen of the catheter adjacent the proximal end thereof.

Preferably, the catheter extends through the inflatable element, and the inflatable element defines with the catheter an annular hollow interior region extending around the catheter, and the inflatable element is located adjacent a distal end of the catheter.

In another embodiment of the invention at least one stimulating electrode is located within the inflatable element on one of the catheter and an inner surface of the inflatable element, and at least one sensing electrode is located within the inflatable element on one of the catheter and the inner surface of the inflatable element axially spaced apart from the at least one stimulating electrode, and a communicating means is provided for facilitating applying a stimulating signal to the at least one stimulating electrode and reading a signal produced on the at least one sensing electrode in response to the stimulating signal applied to the at least one stimulating electrode when the inflatable element is inflated with an electrically conductive inflating medium. Preferably, the communicating means comprises an electrically conducting means extending from the proximal end of the catheter to the respective stimulating and sensing electrodes. Advantageously, a communicating lumen extends through the catheter from the proximal end thereof to the inflatable element for accommodating the electrically conducting means from the proximal end of the catheter to the respective stimulating and sensing electrodes.

In one aspect of the invention two axially spaced apart stimulating electrodes are provided within the inflatable element, and a plurality of axially spaced apart sensing electrodes are located between and axially spaced apart from the stimulating electrodes.

The invention further provides apparatus for determining one of a volume and a transverse cross-sectional area of one of a lumen and a vessel, the apparatus comprising a balloon catheter comprising an elongated catheter extending between a proximal end and a distal end, an inflatable element defining a hollow interior region located on the catheter, a flow lumen extending through the catheter from the proximal end thereof to the inflatable element communicating with the inflatable element, a return lumen extending through the catheter from the proximal end thereof to the inflatable element communicating with the inflatable element, at least one stimulating electrode located within the hollow interior region of the inflatable element on one of the catheter and an inner surface of the inflatable element, at least one sensing electrode located within the hollow interior region of the inflatable element on one of the catheter and the inner surface of the inflatable element axially spaced apart from the at least one stimulating electrode, a communicating means for facilitating applying a stimulating signal to the at least one stimulating electrode and reading a signal produced on the at least one sensing electrode in response to the stimulating signal applied to the at least one stimulating electrode when the inflatable element is inflated with an electrically conductive inflating medium, a system according to the invention for inflating the inflatable element with an electrically conductive liquid inflating medium, the flow line of the system being coupled to the flow lumen of the balloon catheter adjacent the proximal end of the catheter, and the return line of the system being coupled to the return lumen of the balloon catheter at the proximal end of the catheter, a signal generator in communication with the at least one stimulating electrode through the communicating means for applying a stimulating signal to the at least one stimulating electrode, and a signal processing means in communication with the at least one sensing electrode through the communicating means for reading a signal produced on the at least one sensing electrode in response to the stimulating signal applied to the at least one stimulating electrode when the inflatable element is inflated with the electrically conductive liquid inflating medium, the signal processing means being adapted to determine one of the volume and the transverse cross-sectional area of the inflated inflatable element.

In one embodiment of the invention the liquid inflating medium comprises a saline solution.

Additionally the invention provides a balloon catheter comprising an elongated catheter extending between a proximal end and a distal end, an inflatable element defining a hollow interior region located on the catheter, a flow lumen extending through the catheter from the proximal end thereof to the inflatable element communicating with the inflatable element for accommodating an inflating medium thereto during inflating thereof, and a return lumen extending from the proximal end of the catheter to the inflatable element and communicating with the inflatable element for accommodating return of the inflating medium from the inflatable element during deflating of the inflatable element.

The invention also provides a method for inflating an inflatable element with a liquid inflating medium comprising inflating the inflatable element by delivering the liquid inflating medium to the inflatable element through a flow line and simultaneously displacing a gaseous medium in the flow line and the inflatable element to a return line from the inflatable element, deflating the inflatable element by delivering the liquid inflating medium from the inflatable element through the return line along with the gaseous medium to a separating means, separating the liquid inflating medium from the gaseous medium in the separating means, and re-inflating the inflatable element by delivering the separated liquid inflating medium from the separating means through the flow line to the inflatable element.

In one aspect of the invention the method further comprises sequentially deflating the inflatable element by delivering the liquid inflating medium from the inflatable element through the return line along with any remaining gaseous medium to the separating means, separating the liquid inflating medium from the gaseous medium in the separating means, and re-inflating the inflatable element by delivering the separated liquid inflating medium from the separating means through the flow line to the inflatable element until the level of the gaseous medium in the liquid inflating medium has been reduced to a desired level.

In another aspect of the invention the inflatable element is sequentially deflated and inflated until the level of the gaseous medium in the liquid inflating medium has been reduced to a level which permits a true reading of the pressure of the liquid inflating medium in the inflatable element to be obtained from a reading of the pressure of the liquid inflating medium in one of the flow line and the return line.

In one embodiment of the invention the liquid inflating medium is delivered between the separating means and the inflatable element through a valving means, the valving means being operable for selectively and alternately coupling the separating means to the flow line and to the return line.

Preferably, the pressure of the liquid inflating medium in the inflatable element is determined during deflating of the inflatable element by reading the pressure of the liquid inflating medium in the return line. Advantageously, the pressure of the liquid inflating medium in the inflatable element is determined during deflating of the inflatable element by reading the pressure of the liquid inflating medium in the flow line.

The invention further provides a method for inflating an inflatable element of a balloon catheter with a liquid inflating medium, the balloon catheter comprising an elongated catheter extending from a proximal end to a distal end, an inflatable element located on the catheter, a flow lumen extending through the catheter from the proximal end thereof to the inflatable element communicating with the inflatable element for accommodating the liquid inflating medium during inflating of the inflatable element, a return lumen extending through the catheter from the proximal end thereof to the inflatable element communicating with the inflatable element for accommodating the liquid inflating medium during deflating of the inflatable element, the method comprising inflating the inflatable element by delivering the liquid inflating medium to the inflatable element through the flow lumen and simultaneously displacing a gaseous medium in the flow lumen and the inflatable element to the return lumen, deflating the inflatable element by delivering the liquid inflating medium from the inflatable element through the return lumen along with the gaseous medium to a separating means, separating the liquid inflating medium from the gaseous medium in the separating means, re-inflating the inflatable element by delivering the separated liquid inflating medium from the separating means through the flow lumen to the inflatable element.

In one aspect of the invention the method further comprises sequentially deflating the inflatable element by delivering the liquid inflating medium from the inflatable element through the return lumen along with any remaining gaseous medium to the separating means, separating the liquid inflating medium from the gaseous medium in the separating means, and re-inflating the inflatable element by delivering the separated liquid inflating medium from the separating means through the flow lumen to the inflatable element until the level of the gaseous medium in the liquid inflating medium is at a desired level.

In another aspect of the invention the inflatable element is sequentially deflated and inflated until the level of the gaseous medium in the liquid inflating medium has been reduced to a level which permits a true reading of the pressure of the liquid inflating medium in the inflatable element to be obtained from a reading of the pressure of the liquid inflating medium in one of the flow lumen and the return lumen.

In another embodiment of the invention the liquid inflating medium is delivered between the separating means and the inflatable element through a valving means, the valving means being operable for selectively and alternately coupling the separating means to the flow lumen and to the return lumen.

Preferably, the valving means is provided by a first non-return valve located in the return lumen communicating the return lumen with the separating means and being configured to permit flow of the liquid inflating medium through the return lumen from the inflatable element to the separating means.

Advantageously, the valving means is provided by a second non-return valve located in the flow lumen communicating the flow lumen with the separating means and being configured to permit flow of the liquid inflating medium through the return lumen from the separating means to the inflatable element.

In one embodiment of the invention the separating means comprises a reservoir for the liquid inflating medium, the reservoir being configured to permit the gaseous medium to rise through the liquid inflating medium in the reservoir to a top surface of the liquid inflating medium therein. Preferably, the reservoir comprises an elongated barrel of a syringe, the barrel having a communicating port for communicating the barrel with the flow and return lumens.

Preferably, the pressure of the liquid inflating medium in the inflatable element is determined during inflating of the inflatable element by reading the pressure of the liquid inflating medium in the return lumen.

Advantageously, the pressure of the liquid inflating medium in the inflatable element is determined during deflating of the inflatable element by reading the pressure of the liquid inflating medium in the flow lumen.

ADVANTAGES OF THE INVENTION

The advantages of the invention are many. A particularly important advantage of the method and system according to the invention is that it removes substantially all air in or entrained in a liquid inflating medium during inflating of an inflatable element in which air is displaced during inflating thereof. By virtue of the fact that the system and method according to the invention remove substantially all air in or entrained in a liquid inflating medium during inflating of an inflatable element, a true pressure reading of the pressure of the liquid inflating medium in the inflatable element can be obtained from a pressure sensor located either in or remotely of the inflatable element. For example, a true pressure reading of the pressure of the liquid inflating medium within the inflatable element can be obtained by reading the pressure of the liquid inflating medium in either the flow line or the return line remotely of the inflatable element when inflating of the inflatable element has been completed. Additionally, by virtue of the fact that the system and method according to the invention remove substantially all air in or entrained in the liquid inflating medium, a true pressure reading of the pressure of the liquid inflating medium in the inflatable element during inflating of the inflatable element can be obtained from a reading of the pressure of the liquid inflating medium in the return line or lumen remotely of the inflatable element. Furthermore, by virtue of the fact that the system and method according to the invention remove substantially all air in or entrained in the liquid inflating medium, a true pressure reading of the pressure of the liquid inflating medium in the inflatable element during deflating of the inflatable element can be obtained from a reading of the pressure of the liquid inflating medium in the flow line or the flow lumen remotely of the inflatable element.

An additional advantage of the invention is achieved when the inflatable element is used for determining the volume and/or transverse cross-sectional area of a lumen or vessel within which the inflatable element is located. By virtue of the fact that a true pressure reading of the pressure of the liquid inflating medium in the inflatable element can be obtained remotely of the inflatable element, for example, by reading the pressure of the liquid inflating medium in the return line or lumen during inflating of the inflatable element, the pressure of the inflating medium in the inflatable element can be continuously monitored during inflating of the inflatable element, so that a determination can be made as to when the inflatable element has been inflated to a stage where it fills the vessel or lumen within which it is located. Additionally, by reading the pressure of the liquid inflating medium in the flow line or the lumen during deflating of the inflatable element, the pressure of the liquid inflating medium in the inflatable element can be continuously monitored during deflating of the inflatable element.

By providing at least one stimulating electrode within the inflatable element, and at least one sensing electrode in the inflatable element, a relatively accurate determination of the transverse cross-sectional area of the inflatable element can be made. By providing at least two axially spaced apart stimulating electrodes within the inflatable element, and by providing a plurality of axially spaced apart sensing electrodes within the inflatable element between the stimulating electrodes and axially spaced apart therefrom, a relatively accurate determination of the volume of the inflatable element between any two sensing electrodes may be made, and thus, an accurate determination of the volume of a vessel or lumen, or a part of a vessel or lumen within which the inflatable element is located can similarly be made. Furthermore, the provision of a plurality of sensing electrodes allows a relatively accurate determination of the transverse cross-sectional area of the inflatable element to be made at a plurality of correspondingly spaced apart locations of the inflatable element. This, thus, facilitates a relatively accurate determination of the transverse cross-sectional area of a vessel or lumen, or a part of a vessel or lumen within which the inflatable element is located to be made.

BRIEF DESCRIPTION OF THE DRAWINGS

The invention will be more clearly understood from the following description of some preferred embodiments thereof, which are given by way of example only, with reference to the accompanying drawings in which.

DETAILED DESCRIPTION OF THE INVENTION

Figure 1:
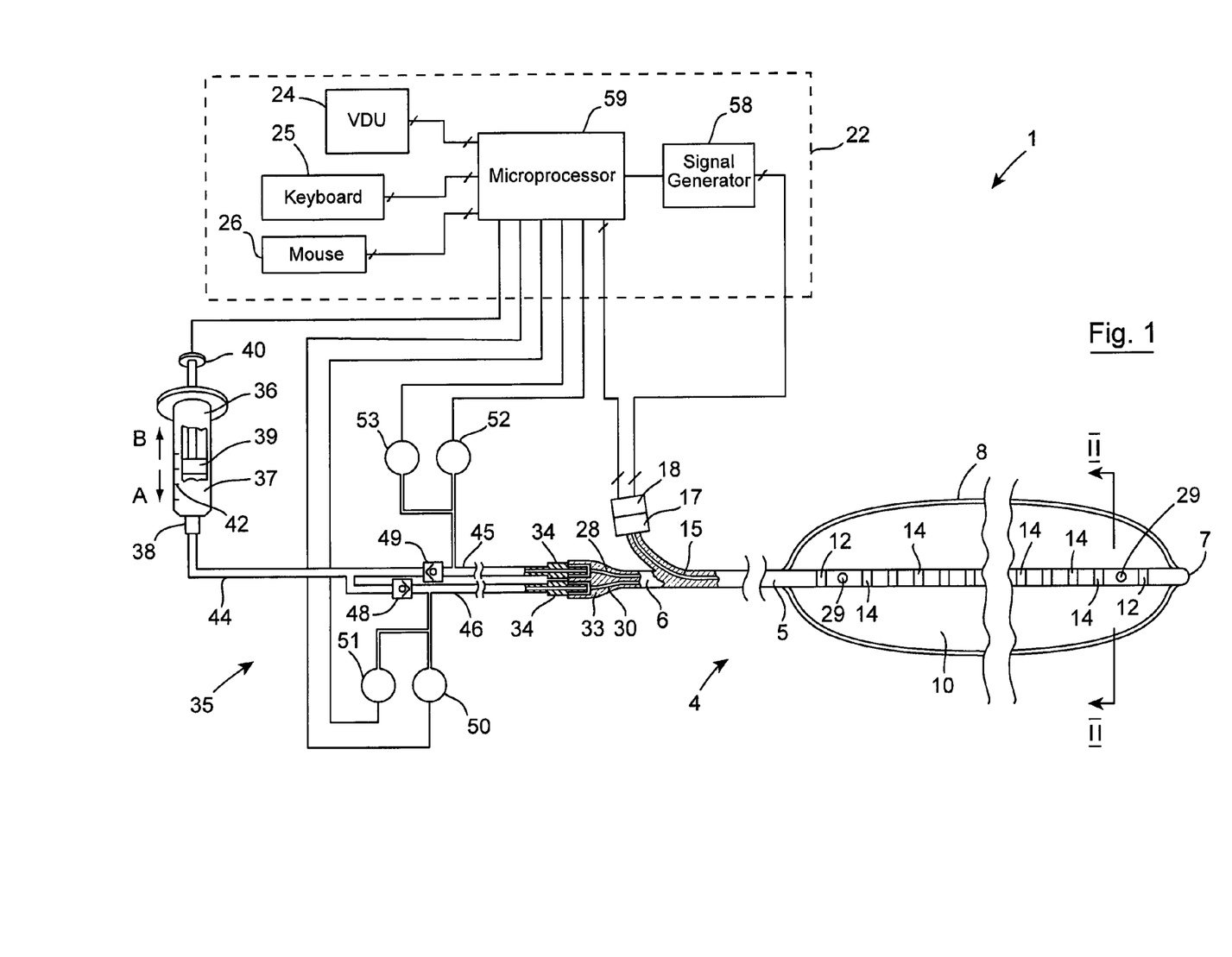
FIG. 1 is a partly block representation, partly schematic representation and partly cross-sectional side elevational view of apparatus according to the invention for determining the volume and the transverse cross-sectional area of a lumen or a vessel which comprises a system also according to the invention for inflating an inflatable element of the apparatus.
Figures 2, 4:
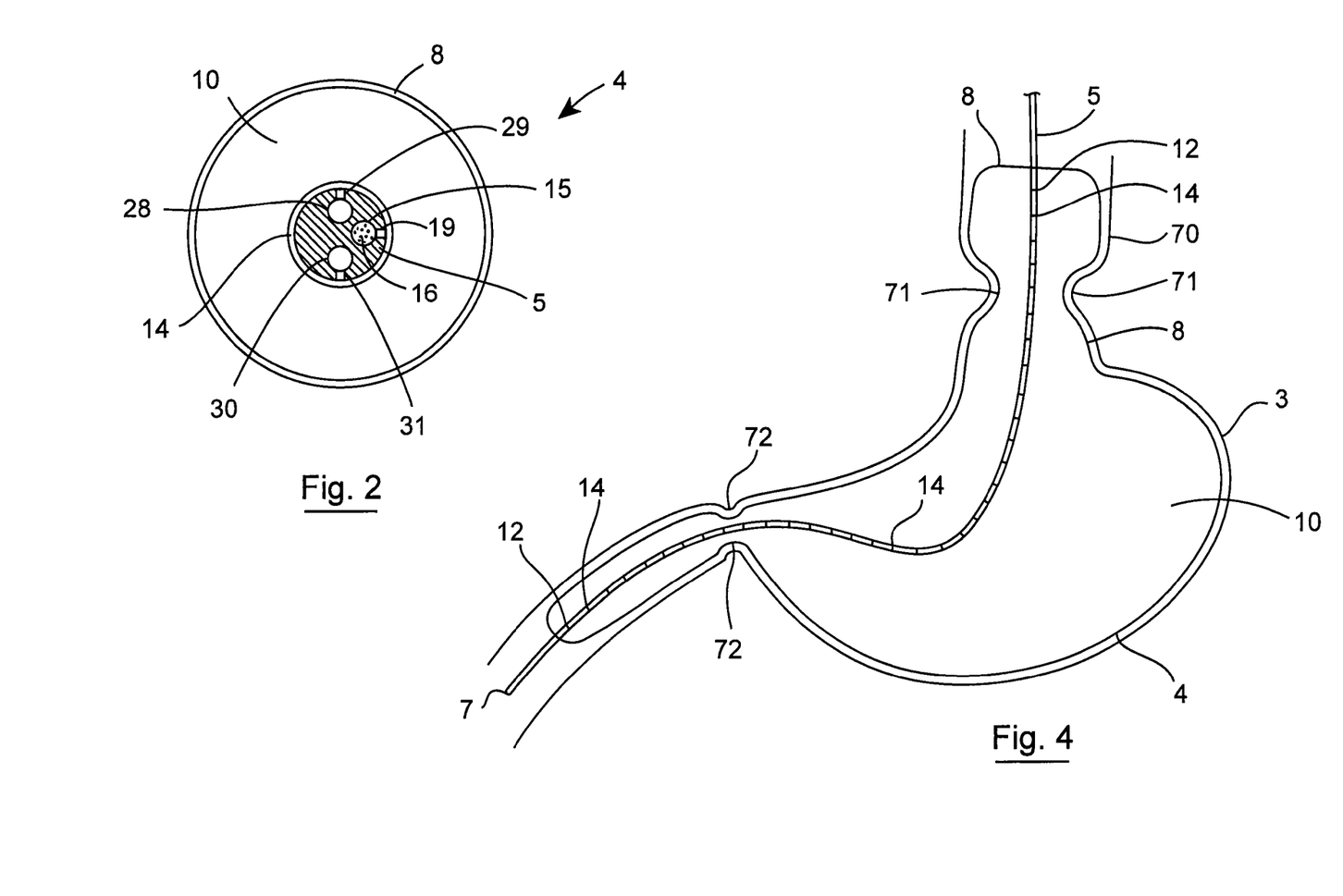
FIG. 2 is a transverse cross-sectional end elevational view of a portion of the apparatus of FIG. 1 on the line II-II of FIG. 1.
FIG. 4 is a side elevational view of a portion of the apparatus of FIG. 1 in use.
Figure 3:
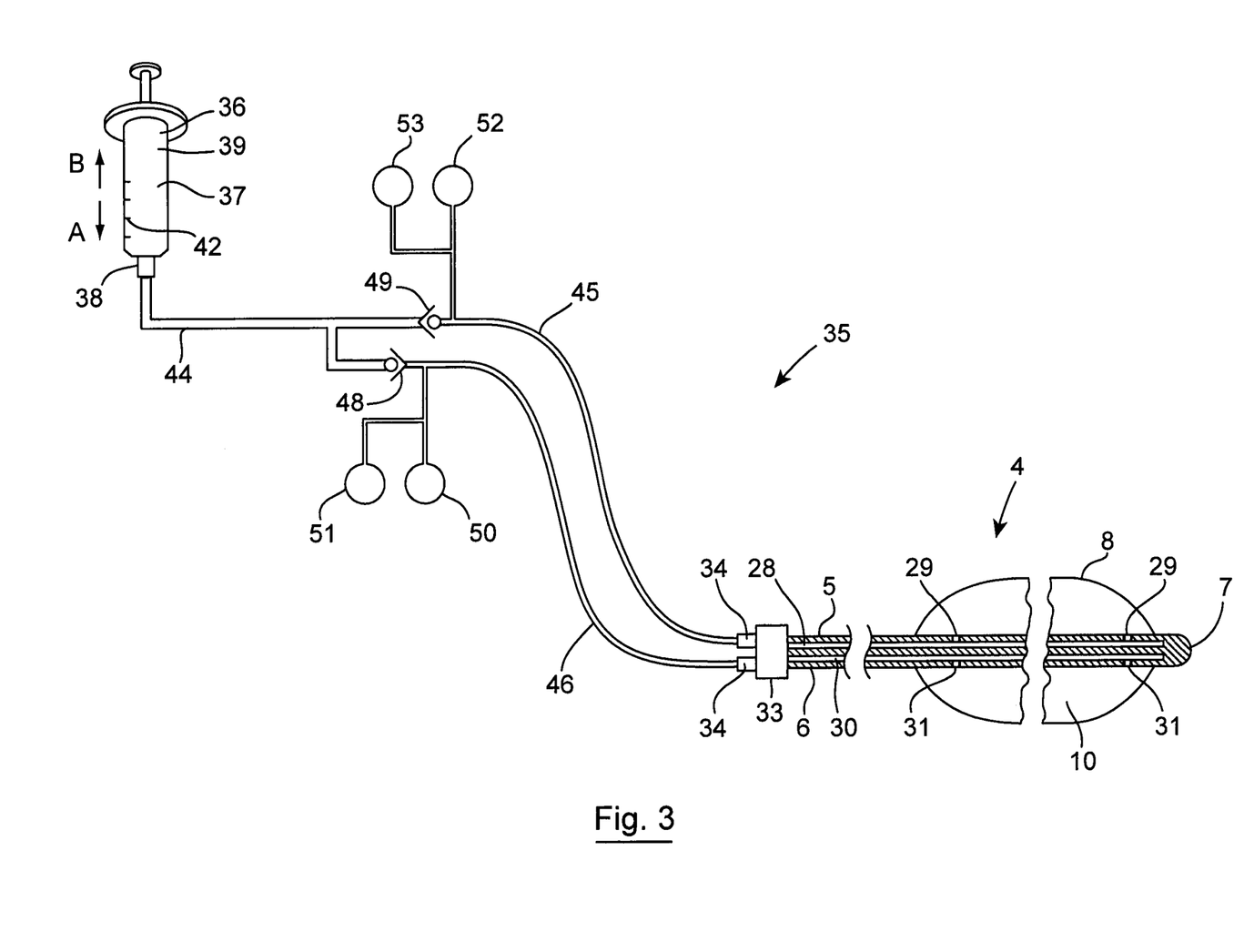
FIG. 3 is a schematic representation of the system of FIG. 1 for inflating the inflatable element of the apparatus of FIG. 1.

Referring to the drawings and initially to FIGS. 1 to 3 thereof, there is illustrated apparatus according to the invention indicated generally by the reference numeral 1 for determining the volume and the transverse cross-sectional area of a lumen or a vessel, such as a biological organ, for example, a stomach 3 of a subject, see FIG. 4, although the apparatus 1 may be used for determining the volume and the transverse cross-sectional area of any lumen or vessel, be it a biological lumen or vessel or otherwise. The apparatus 1 comprises a balloon catheter also according to the invention and indicated generally by the reference numeral 4 which comprises an elongated catheter 5 extending between a proximal end 6 and a distal end 7 and having an inflatable element, namely, a balloon 8 located adjacent the distal end 7. The catheter 5 extends through the balloon 8 adjacent the distal end 7 of the catheter 5 and defines with the balloon 8 an annular hollow interior region 10 extending around the catheter 5. The balloon catheter 4 is adapted for inserting into the stomach 3 of the subject or a pouch formed in the stomach by bariatric surgery with the balloon 8 located in the stomach 3 or the pouch formed in the stomach. The balloon 8 is inflatable as will be described below by a liquid inflating medium, which in this case is an electrically conductive liquid medium, such as a saline solution, to define the interior volume of the stomach 3, so that the volume of the stomach 3 can be determined, as will also be described below. The balloon 8 is adapted so that in its unrestrained inflated state it is of circular transverse cross-section, and of substantially cylindrical configuration, defining a central longitudinally extending central axis, which coincides with the longitudinal central axis of the catheter 5.

A pair of stimulating electrodes 12 for receiving an electric current stimulus signal of known constant value are located axially spaced apart on the catheter 5 within the hollow interior region 10 of the balloon 8. A plurality of axially spaced apart sensing electrodes 14 are located on the catheter 5 between and axially spaced apart from is the stimulating electrodes 12 on which voltage signals are produced in response to the stimulus signal applied to the stimulating electrodes 12 when the balloon 8 is inflated with the electrically conductive liquid inflating medium. The voltage signals produced on the sensing electrodes 14 are indicative of the transverse cross-sectional area of the balloon 8 adjacent the respective sensing electrodes 14 when the balloon 8 is inflated with the electrically conductive liquid inflating medium. The stimulating electrodes 12 and the sensing electrodes 14 in this embodiment of the invention are band electrodes which extend completely around the catheter 5.

A wire accommodating lumen 15 extending through the catheter 5 accommodates a communicating means, namely, a plurality of mutually insulated wires 16 from corresponding ones of the stimulating electrodes 12 and the sensing electrodes 14 to a multi-pin socket connector 17 at the proximal end 6 of the catheter 5. Wire accommodating bores 19 extending radially through the catheter 5 within the balloon 8 accommodate the wires 16 from the wire accommodating lumen 15 to the respective stimulating and sensing electrodes 12 and 14. A multi-pin plug connector 18 coupled to the socket connector 17 couples the wires 16 and in turn the stimulating electrodes 12 and the sensing electrodes 14 to a monitoring and control unit 22 for controlling the operation of the balloon catheter 4 for determining the volume and the transverse cross-sectional area of the balloon 8 as will be described below.

A visual display means, namely, a visual display screen 24 coupled to the monitoring and control unit 22 displays an approximate visual representation of a cross-section of the inflated balloon 8 as will also be described below. A keyboard 25 and a mouse 26 coupled to the monitoring and control unit 22 are provided for facilitating inputting of signals and commands to the monitoring and control unit 22 for controlling operation of the balloon catheter 4 for determining the volume and the transverse cross-sectional area of the balloon 8 and in turn the stomach 3.

A flow lumen 28 extends through the catheter 5 from the proximal end 6 to the balloon 4 and communicates with the balloon 4 through radially extending flow bores 29 for accommodating the liquid inflating medium into the balloon 8 for inflating thereof. A return lumen 30 also extends through the catheter 5 from the proximal end 6 thereof to the balloon 8 and communicates with the balloon 8 through radially extending return bores 31 for accommodating the liquid inflating medium from the balloon 8 during deflating of the balloon 8 as will be described below. The flow lumen 28 and the return lumen 30 terminate in a coupler 33 adjacent the proximal end 6 of the catheter 5.

A system also according to the invention and indicated generally by the reference numeral 35 for inflating the balloon 8 of the balloon catheter 4 with the liquid inflating medium comprises a pump means, which in this embodiment of the invention comprises a syringe 36. The syringe 36 comprises a syringe barrel 37 of circular transverse cross-section, which acts as a reservoir for the liquid inflating medium. The syringe barrel 37 terminates in a communicating port 38 through which the liquid inflating medium is accommodated during inflating and deflating of the balloon 8. A piston 39 carried on a distal end of a handle 40 is slideable within the syringe barrel 37 in a first direction in the direction of the arrow A into the syringe barrel 37 towards the communicating port 38 for discharging the liquid inflating medium from the syringe barrel 37 to the balloon 8 for inflating thereof, and in a second direction in the direction of the arrow B outwardly of the syringe barrel 37 for drawing the liquid inflating medium into the syringe barrel 37 from the balloon 8 for deflating the balloon 8.

In this embodiment of the invention the syringe barrel 37 is configured with the syringe barrel 37 vertically orientated so that when the piston 39 is being urged in the first direction in the direction of the arrow A, the piston 39 is moved vertically downwardly within the syringe barrel 37, and when the piston 39 is being urged in the second direction in the direction of the arrow B, the piston 39 is moved vertically upwardly within the syringe barrel 37. In this way the top surface of the liquid inflating medium in the syringe barrel 37 interfaces with the piston 39 so that any gaseous medium, typically, air in the liquid inflating medium rises through the liquid inflating medium in the syringe barrel 37 to the top surface thereof so that such gaseous medium is trapped between the top surface of the liquid inflating medium in the syringe barrel 37 and the piston 39. Accordingly, the syringe 36 as well as acting as a reservoir for the liquid inflating medium and a pump means for delivering and withdrawing the liquid inflating medium to and from the balloon 8, also acts as a separating means for separating the liquid inflating medium from gaseous medium in or entrained in the liquid inflating medium.

A graduated scale 42 on the syringe barrel 37 is provided for indicating the volume of liquid inflating medium in the syringe barrel 37 or discharged therefrom.

A main fluid line 44 extending from the communicating port 38 of the syringe barrel 37 communicates the syringe barrel 37 with a flow line 45 and a return line 46 which are connected to the flow lumen 28 and the return lumen 30, respectively, through couplers 34 which sealably engage the coupler 33. The main fluid line 44 is connected to the flow line 45 and the return line 46 by a valving means which comprises a first non-return valve 48 in the return line 46, and a second non-return valve 49 in the flow line 45. The first non-return valve 48 is configured to permit return flow of the liquid inflating medium from the balloon 8 to the syringe 36 through the return line 46 and the return lumen 30, and to prevent flow of the liquid inflating medium from the syringe 36 to the balloon 8 through the return lumen 30 and the return line 46. The second non-return valve 49 is configured to permit flow of the liquid inflating medium from the syringe 36 to the balloon 8 through the flow lumen 28 and the flow line 45, and to prevent flow of the liquid inflating medium from the balloon 8 to the syringe 36 through the flow line 45 and the flow lumen 28.

A pressure sensing means for monitoring the pressure of the liquid inflating medium in the balloon 8 and in the flow and return lines 45 and 46 comprises a first pressure sensing means provided by a first main pressure sensor 50 and a first secondary pressure sensor 51, and a second pressure sensing means provided by a second main pressure sensor 52 and a second secondary pressure sensor 53. The first main pressure sensor 50 is a fine pressure sensor, and the first secondary pressure sensor 51 is a coarse pressure sensor. Both the first main pressure sensor 50 and the first secondary pressure sensor 51 are coupled to the return line 46 adjacent the first non-return valve 48 for monitoring the pressure of the liquid inflating medium in the return line 46. The second main pressure sensor 52 is a fine pressure sensor, and the second secondary pressure sensor 53 is a coarse pressure sensor. Both the second main pressure sensor 52 and the second secondary pressure sensor 53 are coupled to the flow line 45 adjacent the second non-return valve 49 for monitoring the pressure of the liquid inflating medium in the flow line 45.

The monitoring and control unit 22 is coupled to the first main pressure sensor 50, the first secondary pressure sensor 51, the second main pressure sensor 52 and the second secondary pressure sensor 53 for reading signals from the respective first and second main and secondary pressure sensors 50, 51, 52 and 53 which are indicative of the pressure monitored by the respective pressure sensors 50 to 53. The monitoring and control unit 22 reads the signals from the first main pressure sensor 50 and the second secondary pressure sensor 53 during inflating of the balloon 8 by the syringe 36. The signals read from the first main pressure sensor 50 during inflating of the balloon 8 are indicative of the pressure of the liquid inflating medium in the balloon 8 during inflating thereof. The signals read from the second secondary pressure sensor 53 during inflating of the balloon 8 are indicative of the pressure at which the liquid inflating medium is being delivered by the syringe 36. The monitoring and control unit 22 determines the pressure of the liquid inflating medium in the balloon 8 during inflating thereof from the signals read from the first main pressure sensor 50, and also determines the pressure at which the liquid inflating medium is being delivered by the syringe 36 during inflating of the balloon 8 from the signals read from the second secondary pressure sensor 53. The monitoring and control circuit 22 reads signals from the first secondary pressure sensor 51 and the second main pressure sensor 52 during deflating of the balloon 8 by the syringe 36. The signals read from the second main pressure sensor 52 during deflating of the balloon 8 are indicative of the pressure of the liquid inflating medium in the balloon 8 during deflating thereof. The signals read from the first secondary pressure sensor 51 during deflating of the balloon 8 are indicative of the pressure at which the liquid inflating medium is being drawn into the syringe 36 during deflating of the balloon 8. The monitoring and control unit 22 determines the pressure of the liquid inflating medium in the balloon 8 during deflating thereof from the signals read from the second main pressure sensor 52, and also determines the pressure at which the liquid inflating medium is being drawn into the syringe 36 during deflating of the balloon 8 from the signals read from the first secondary pressure sensor 51.

By reading the pressure of the liquid inflating medium in the flow line 45 from the second secondary pressure sensor 53 during inflating of the balloon 8, the monitoring and control circuit 22 can detect a blockage in any of the flow and return lines 45 and 46 and the flow and return lumens 28 and 30. A blockage in any of the flow and return lines 45 and 46 and the flow and return lumens 28 and 30 during inflating of the balloon 8 would be detected by an unusual rise in the pressure read from the second secondary pressure sensor 53. By reading the pressure of the liquid inflating medium in the return line 46 from the first secondary pressure sensor 51 during deflating of the balloon 8, the monitoring and control circuit 22 can detect a blockage in any of the flow and return lines 45 and 46 and the flow and return lumens 28 and 30. A blockage in any of the flow and return lines 45 and 46 and the flow and return lumens 28 and 30 would be detected by an unusual fall in the pressure read from the first secondary pressure sensor 51.

In this embodiment of the invention, since the apparatus 1 is provided for determining the volume and the transverse cross-sectional area of a vessel or a lumen, the pressure at which the balloon 8 is inflated during a procedure for determining the volume and/or transverse cross-sectional area of a vessel or lumen is relatively low. This is because the balloon 8 during such a procedure only has to be inflated to a state where it fills the vessel or lumen, the volume and/or transverse cross-sectional area of which is to be determined. Accordingly, the balloon catheter 4 in this embodiment of the invention is a relatively low pressure balloon catheter. The first main pressure sensor 50 has a workable pressure range of −50 millibars to +200 millibars. Thus, the first secondary pressure sensor 51 has a workable pressure range from −1,000 millibars to +1,000 millibars. The second main pressure sensor 52 has a workable range of −50 millibars to 200 millibars, while the second secondary pressure sensor 53 has a workable pressure range from 0 millibars to +1,000 millibars.

However, the apparatus 1 according to the invention and the balloon catheter 4 also according to the invention may be provided for dilating an occlusion in a vessel or a lumen, or for ablating an occlusion in a vessel or lumen. In the latter case, one or more ablating electrodes would be provided on the outer circumferential surface of the balloon 8 of the balloon catheter 4 for carrying out the ablating procedure. In either of these cases, the balloon catheter would have to operate at a relatively high pressure, and accordingly, the first main and secondary pressure sensors 50 and 51, and the second main and secondary pressure sensors 52 and 53 would be provided to operate at appropriate workable pressure ranges. Similarly, where the apparatus 1 according to the invention and the balloon catheter 4 according to the invention are provided for other high pressure operations, the first main and secondary pressure sensors 50 and 51 and the second main and secondary pressure sensors 52 and 53 would also be provided to have an appropriate workable pressure range.

Before describing the remainder of the apparatus 1, the operation of the syringe 36 for inflating the balloon 8 with the liquid inflating medium and for separating the liquid inflating medium from any gaseous medium, namely, air in the system 35 and in the balloon catheter 4 will first be described. By separating the liquid inflating medium from air in the system 25 and the balloon catheter 4, so that the balloon 8 when inflated as well as the flow and return lumens 28 and 30, and the flow and return lines 45 and 46 only contain liquid inflating medium, the pressure monitored by the first main pressure sensor 50 produces a true reading of the pressure of the liquid inflating medium in the balloon 8 during inflating of the balloon 8, and the second main pressure sensor 52 produce a relatively true pressure of the liquid inflating medium in the balloon 8 during deflating of the balloon 8.

Initially the syringe barrel 37 is fully charged with the liquid inflating medium by drawing liquid inflating medium from a suitable source (not shown) into the syringe barrel 37 through the communicating port 38 by the piston 39 while the syringe 36 is disconnected from the main fluid line 44 and is connected to the suitable source. On the syringe barrel 37 being fully charged with the liquid inflating medium, the syringe 36 is disconnected from the suitable source, and is connected to the main fluid line 44. The piston 39 is moved in the first direction, namely, in the direction of the arrow A for discharging the liquid inflating medium from the syringe barrel 37 through the main line 44 and in turn through the flow line 45 and the flow lumen 28 to the balloon 8 for inflating thereof.

As the liquid inflating medium is being discharged from the syringe 36 to the balloon 8, air in the first flow line 45, the first lumen 28 and the balloon 8 is simultaneously displaced into the return lumen 30 and the return line 46. With the balloon 30 inflated, the piston 39 is urged in the second direction, namely, the direction of the arrow B for drawing the liquid inflating medium from the balloon 8 through the return lumen 30 and the return line 46 for deflating the balloon 8. As the liquid inflating medium is being drawn from the balloon 8 into the syringe 36, air in the return lumen 30 and the return line 46 along with the liquid inflating medium is drawn into the syringe barrel 37. The air which is drawn into the syringe barrel 37, whether it is entrained in the liquid inflating medium or otherwise, rises to the top surface of the liquid inflating medium in the syringe barrel 37, and is entrapped between the piston 39 and the top surface of the liquid medium in the syringe barrel 37.

At this stage the piston 39 is again urged in the first direction, namely, in the direction of the arrow A to deliver the liquid inflating medium in the syringe barrel 37 through the flow line 45 and the flow lumen 28 to re-inflate the balloon 8. Any residual air in the flow line 45, the flow lumen 28 and the balloon 8 during re-inflating of the balloon 8 is discharged into the return lumen 30 and the return line 46. During re-inflating of the balloon 8 the piston 39 is urged in the first direction in the direction of the arrow A until only a small amount of liquid inflating medium remains in the lower end of the syringe barrel 37 adjacent the communicating port 38. At which stage operation of the piston 39 ceases in order to avoid any danger of the air entrapped between the piston 39 and the top surface of the liquid inflating medium in the syringe barrel 37 being discharged into the main fluid line 44.

Again the balloon 8 is deflated by operating the piston 39 in the second direction, namely, in the direction of the arrow B to draw the liquid inflating medium from the balloon 8 through the return lumen 30 and the return line 46 to the syringe 36. At this stage any residual air in the balloon 8 and the return lumen 30 and the return line 46 after the previous inflating the balloon 8 is drawn along with the liquid inflating medium into the syringe barrel 37. The residual air rises through the liquid inflating medium in the syringe barrel 37 to the top thereof and is entrapped with the air already entrapped between the piston 39 and the top surface of the liquid inflating medium in the syringe barrel 37.

Again the balloon 8 is re-inflated with the liquid inflating medium by urging the piston 39 in the first direction, namely, in the direction of the arrow A for discharging the liquid inflating medium in the syringe barrel 37 into the balloon 8 through the flow line 45 and the flow lumen 28. Again, when re-inflating the balloon 8 the piston 39 is operated in the direction of the arrow A until only a small amount of the liquid inflating medium remains in the lower end of the syringe barrel 37 adjacent the communicating port 38, and further operation of the piston 39 ceases in order to avoid any danger of the air entrapped between the piston 39 and the top surface of the liquid inflating medium in the syringe barrel 37 entering the main fluid line 44.

At this stage the balloon 8 should be inflated with the liquid inflating medium, and all the air should have been extracted from the balloon 8, the flow and return lumens 28 and 30 and the flow and return lines 45 and 46 as well as the main fluid line 44. However, if it is felt that residual air still remains in the balloon 8, the flow and return lumens 28 and 30 or the flow and return lines 45 and 46 or the main fluid line 44, the balloon 8 can be again deflated and re-inflated with the liquid inflating medium as just described. This sequence of deflating and re-inflating cycles of the balloon 8 with the liquid inflating medium may continue until all residual air has been removed from the balloon 8, the flow and return lumens 28 and 30, the flow and return lines 45 and 46 and the main fluid line 48, or until the level of residual air remaining in the balloon 8, the flow and return lumens 28 and 30, the flow and return lines 45 and 46 and the main fluid line 44 is sufficiently low that the pressure values read from the first and second main pressure sensors 50 and 52 as described above are true values of the pressure of the liquid inflating medium in the balloon 8 during inflating and deflating thereof, as the case may be.

Once the air has been removed from the balloon 8, the flow and return lumens 28 and 30 and the flow and return lines 45 and 46, the pressure read from the first main pressure sensor 50 should be a true reading of the pressure of the liquid inflating medium in the balloon 8 during inflating thereof, and the pressure read from the second main pressure sensor 52 should be a true reading of the pressure of the liquid inflating medium in the balloon 8 during deflating of the balloon 8. Once the balloon 8 has been inflated, and inflating thereof has terminated, the pressures read from the first and second main pressure sensors 50 and 52 should be substantially similar and should be a true reading of the pressure of the liquid inflating medium in the balloon 8.

By monitoring the pressure of the liquid inflating medium on the first main pressure sensor 50 during inflating of the balloon 8, a relatively accurate determination can be made as to when the balloon 8 has been inflated to a state where it fills the lumen or vessel, or in other words, defines the interior of the lumen or vessel within which the balloon 8 is located. It has been found that during inflating of the balloon 8 with the liquid inflating medium, the pressure of the liquid inflating medium in the balloon 8 remains substantially constant, or the rate of change of pressure of the liquid inflating medium in the balloon 8 per unit volume of liquid inflating medium delivered into the balloon 8 remains substantially constant, until the balloon 8 has been inflated to the state where it fills the lumen or vessel within which it is located. At that stage the pressure of the balloon 8 on the inner wall of the lumen or vessel resulting from further inflating of the balloon causes the pressure of the liquid inflating medium in the balloon 8 to increase, or alternatively, causes the rate of change of the pressure in the liquid inflating medium per unit volume of the liquid inflating medium delivered into the balloon 8 to increase. Thus, by monitoring the pressure of the liquid inflating medium in the balloon 8 which is read from the first main pressure sensor 50, during inflating of the balloon 8, a determination can be made as to when the balloon 8 has been inflated to a state where it fills the lumen or vessel, in other words, defines the interior of the lumen or vessel within which it is located.

The volume of the syringe barrel 37 is such as to contain sufficient liquid inflating medium, so that when the balloon 8 has been inflated to its maximum volume with the flow and return lumens 28 and 30 and the flow and return lines 45 and 46 as well as the main fluid line 44 filled with the liquid inflating medium, there is still liquid inflating medium remaining in the barrel 37 of the syringe 36.

Returning now to the monitoring and control unit 22, the monitoring and control unit 22 comprises a signal generator 58 for generating the constant current signal of known current for applying to the stimulating electrodes 12. A signal processing means, namely, a microprocessor 59 is programmed for operating the signal generator 58 to generate the constant current signal, and to simultaneously read voltage signals produced on the sensing electrodes 14 in response to the constant current signal on the stimulating electrodes 12 when the balloon 8 is inflated with the liquid inflating medium, which as discussed above, is an electrically conductive medium. The microprocessor 59 is also programmed for determining the transverse cross-sectional area of the inflated balloon 8 adjacent the respective sensing electrodes 14 from the voltages read from the sensing electrodes 14, and to determine the volume of the inflated balloon 8. The computation of the transverse cross-sectional area of the balloon 8 adjacent the respective sensing electrodes 14 from the voltages produced on the sensing electrodes 14 and the computation of the volume of the inflated balloon 8 from the voltages produced on the sensing electrodes 14 will be understood by those skilled in the art, and is disclosed in PCT Published Application Specification No. WO 2009/001328.

Where it is desired to determine the volume of the inflated balloon 8 between the extreme-most sensing electrodes 14, the volume is determined by computing the volumes of the inflated balloon 8 between adjacent sensing electrodes 14 by multiplying the computed transverse cross-sectional area adjacent each sensing electrode 14 by the spacing between that sensing electrode 14 and the next adjacent sensing electrodes 14. The total volume of the inflated balloon 8 between the extreme-most sensing electrodes 14 is determined by summing the computed volumes of the balloon 8 between the respective adjacent sensing electrodes 14.

Similarly, the volume of the inflated balloon 8 between any pair of sensing electrodes 14 may be computed by summing the volumes computed between the adjacent sensing electrodes 14 which are located between the two sensing electrodes 14 between which the volume of the inflated balloon 8 is to be determined. The microprocessor 59 is programmed to compute the volume of the inflated balloon 8 between any pair of selected sensing electrodes 14.

Figure 5:
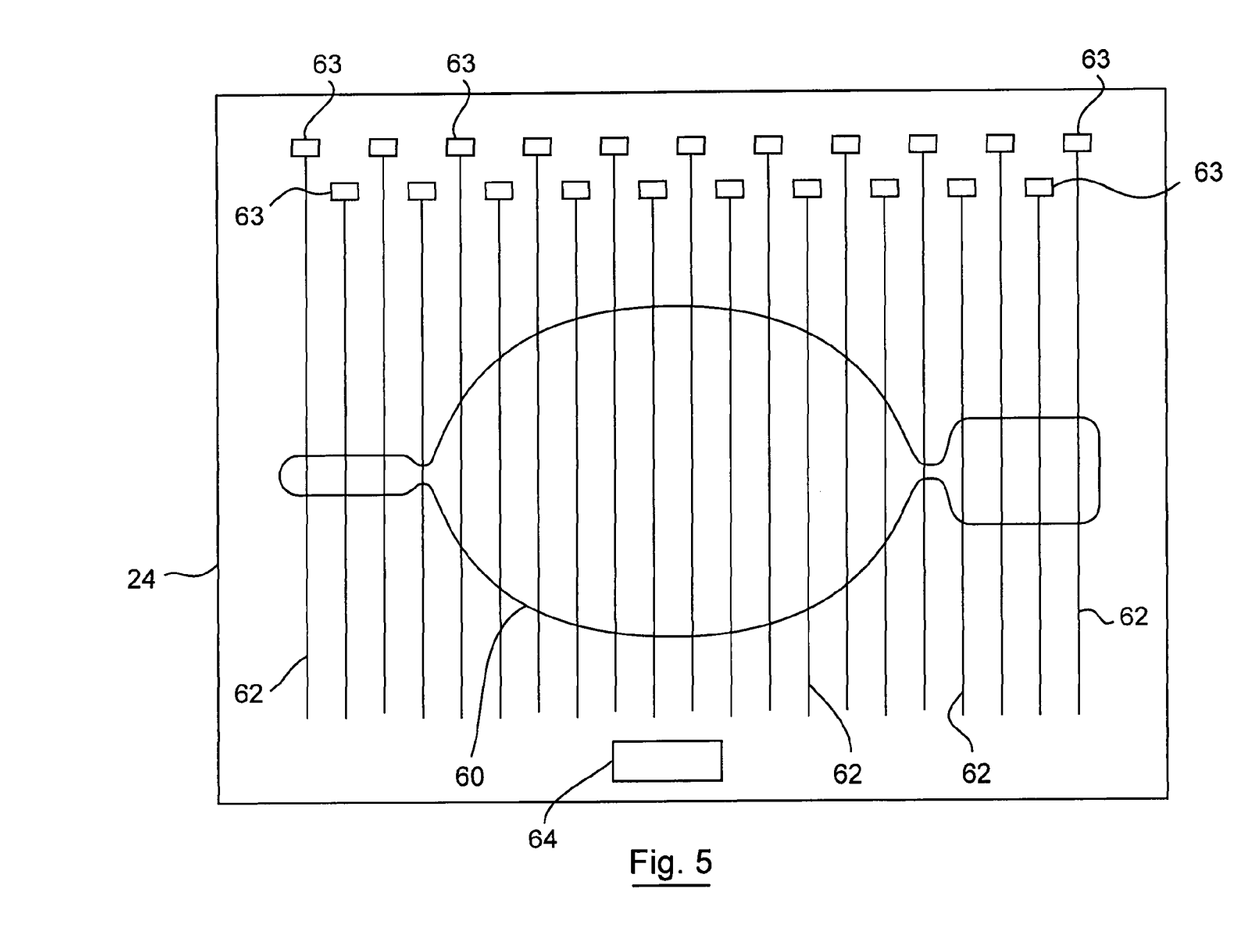
FIG. 5 is a graphical representation of a typical approximate longitudinal cross-section of the inflatable element when inflated displayed on a visual display screen of the apparatus of FIG. 1.

The microprocessor 59 is appropriately programmed to operate the visual display screen 24 to display the value of the volume of the inflated balloon 8 between any selected pair of sensing electrodes 14. The microprocessor 59 is also programmed to operate the visual display screen 24 to graphically display a graphical representation of an approximate longitudinal cross-section of the inflated balloon 8 between the extreme-most sensing electrodes 14, with a representation of the locations of the sensing electrodes 14 superimposed thereon for facilitating selection of any pair of the sensing electrodes between which the volume of the balloon is to be computed. The microprocessor 59 also is programmed to operate the visual display screen 24 to display the transverse cross-sectional area of the inflated balloon 8 adjacent the respective sensing electrodes 14. A typical display of a graphical representation 60 of an approximate longitudinal cross-section of the inflated balloon 8 when inflated which is displayed on the visual display screen 24 is illustrated in FIG. 5. The locations of the sensing electrodes 14 are represented by lines 62 superimposed on the graphical representation 60 of the inflated balloon 8.

The transverse cross-sectional area of the inflated balloon 8 at the respective sensing electrodes 14 is displayed in the windows 63 corresponding to the lines 62. The volume of the inflated balloon 8 between any selected pair of the sensing electrodes 14 is displayed in a window 63.

It is envisaged that the visual display screen 24 may be a touch screen, and in which case, the pair of sensing electrodes 14 between which the volume of the balloon 8 is to be determined would be selected by touching the relevant pair of lines 62 representative of the two sensing electrodes 14 between which the volume of the inflated balloon 8 is to be determined. Alternatively, the lines 62 representative of the pair of sensing electrodes 14 between which the volume of the inflated balloon 8 is to be determined may be selected by moving a cursor on the visual display screen 24 to the relevant lines 62 and selecting the lines 62 by the mouse 26. In another alternative embodiment of the invention the lines 62 representative of the sensing electrodes 14 may be numbered, and the identifying numbers of the lines 62 representative of the pair of sensing electrodes 14 between which the volume of the inflated balloon 8 is to be determined would be inputted by keying in the identification numbers of the respective lines 62 via the keyboard 25.

The microprocessor 59 is programmed to read signals from the first and second main and secondary pressure sensors 50, 51, 52 and 53 during inflating and deflating of the balloon 8 by the syringe 36, and to control the operation of the syringe 36 in response to pressure values read from the pressure sensors 50, 51, 52 and 53. A linear motor (not shown) operates the handle 40 and the piston 39 of the syringe 36 for inflating and deflating the balloon 8 under the control of the microprocessor 59. The microprocessor 59 also operates the visual display screen 24 to display the pressure values read from the first and second main and secondary pressure sensors 50, 51, 52 and 53, which are continuously updated during inflating and deflating of the balloon 8. The microprocessor 59 is programmed to sound an alarm in the event of a blockage being detected in any of the flow and return lines and lumens 45, 46 and 28 and 30, and to deactivate the linear motor (not shown) which operates the syringe 36. The microprocessor 59 is also programmed to display a message indicating the detection of the blockage on the visual display screen 24.

Use of the apparatus 1 for determining the volume and the transverse cross-sectional area of the stomach 3 of a human subject will now be described with reference to FIG. 4. The distal end 7 of the balloon catheter 4 with the balloon 8 deflated is entered nasally or orally into the oesophagus 70 of the subject and is urged downwardly through the oesophagus 70 and through the lower oesophageal sphincter 71 into the stomach 3 until the distal end of the balloon 8 passes through the lower sphincter 72 of the stomach 3. At this stage the balloon 8 should be located within the stomach 3 of the subject with the distal end thereof projecting through the lower sphincter 72 and the proximal end thereof projecting through the lower oesophageal sphincter 71. The balloon 8 is then inflated with the liquid inflating medium as already described under the control of the microprocessor 59. Initially the syringe 36 is charged with the liquid inflating medium while the communicating port 38 of the syringe barrel 37 is disconnected from the main fluid line 44 and connected to the suitable source of the liquid inflating medium. With the communicating port 38 of the syringe 36 reconnected to the main fluid line 44, the piston 39 is operated under the control of the microprocessor 59 for delivering the liquid inflating medium from the syringe 36 to the balloon 8 for inflating thereof. As the liquid inflating medium passes through the flow line 45 and the flow lumen 28 into the balloon 8, air located therein is displaced into the return lumen 30 and the return line 46.

The piston 39 of the syringe 36 is then operated under the control of the microprocessor 59 to deflate the balloon 8 by drawing the liquid inflating medium and the air from the balloon 8 through the return lumen 30 and the return line 46. Air drawn into the syringe 36 is separated therein with the air being entrapped between the piston 39 and the top surface of the liquid inflating medium. The balloon 8 is then re-inflated by operating the piston 39 of the syringe 36 under the control of the microprocessor 59 to urge the liquid inflating medium from the syringe 36 to the balloon 8 through the flow line 45 and the flow lumen 28, thereby further displacing any residual air in the flow lumen 28, the flow line 45 and the balloon 8 into the return lumen 30 and the return line 46. Again the balloon is deflated by operating the piston 39 under the control of the microprocessor 59 to draw the liquid inflating medium together with any residual air remaining in the balloon 8, the return lumen 30 and the return line 46 into the syringe 36, where the residual air is again separated from the liquid inflating medium. The piston 39 is again operated under the control of the microprocessor 59 for delivering the liquid inflating medium from the syringe 36 to the balloon 8 for inflating thereof through the flow line 45 and the flow lumen 28.

If at this stage the level of any residual air remaining in the balloon 8, the flow and return lumens 28 and 30 and the flow and return lines 45 and 46 is such as to prevent a true reading of the pressure of the liquid inflating medium in the balloon 8 being obtained from the appropriate one of the first and second main pressure sensors 50 and 52, depending on whether the balloon 8 is being inflated or deflated, a further cycle of deflating the balloon 8 and re-inflating the balloon 8 is carried out as already described under the control of the microprocessor 59. Further cycles of deflating and re-inflating the balloon 8 may be carried out until substantially all of the residual air in the liquid inflating medium has been separated and displaced from the liquid inflating medium, or at least until the level of any residual air in the liquid inflating medium in the balloon 8, the flow and return lumens 28 and 30 and the flow and return lines 45 and 46 is at a level which permits a true reading of the pressure of the liquid inflating medium in the balloon 8 to be obtained from the appropriate one of the first and second main pressure sensors 50 and 52. Once substantially all the residual air has been displaced from the liquid inflating medium in the balloon 8, the flow and return lumens 28 and 30 and the flow and return lines 45 and 46, or once the level of residual air remaining in the liquid inflating medium in the balloon 8, the flow and return lumens 28 and 30 and the flow and return lines 45 and 46 is at a level which permits a true reading of the pressure of the liquid inflating medium in the balloon 8 to be read from the appropriate one of the first and second main pressure sensors 50 and 52, operation of the balloon catheter 4 under the control of the microprocessor 59 continues as follows.

Further inflating of the balloon 8 is carried out by the syringe 36 under the control of the microprocessor 59 until the pressure read from the first main pressure sensor 50 is indicative of the balloon 8 being inflated to a stage where it fills the stomach 3, in other words, to a stage where the inflated balloon 8 defines the interior of the stomach 3. At that stage the microprocessor 59 operates the signal generator 58 to apply the constant current signal to the stimulating electrodes 12, and the voltage signals produced on the sensing electrodes 14 in response to the constant current signal are read by the microprocessor 59, which then in turn computes the transverse cross-sectional area values of the balloon 8 adjacent the respective sensing electrodes 14, and produces the graphical representation 60 of the approximate longitudinal cross-section of the balloon 8 which is displayed on the visual display screen 24 with the lines 62 representative of the sensing electrodes 14 superimposed thereon. The microprocessor 59 also operates the visual display screen 24 for displaying the values of the transverse cross-sectional area of the balloon 8 in the window 63 adjacent the respective sensing electrodes 14. The lines 62 representative of the sensing electrodes 68 between which the volume of the balloon is to be computed corresponding to the stomach 3 are selected as already described and the microprocessor 59 computes the volume which is displayed in the window 64.

When the volume of the stomach has been computed, and any other data which is required has been obtained, the balloon 8 is deflated by operating the syringe 36 under the control of the microprocessor 59 to draw the liquid inflating medium from the balloon 8 through the return lumen 46 and the return line 46. The balloon catheter 4 is then withdrawn through the oesophagus 70 and removed from the subject.

At any stage during inflating or deflating of the balloon 8 the microprocessor 59 determines from the signals read from the second and first secondary pressure sensors 53 and 51, respectively, that any one of the flow and return lines 45 and 46 and the flow and return lumens 28 and 30 are blocked, the microprocessor 59 deactivates the linear motor which operates the syringe 36, thereby terminating inflating or deflating of the balloon 8, sounds an alarm and operates the visual display screen 24 to display a message indicating the detection of the blockage.

It is also envisaged that during inflating and/or deflating of the balloon 8, the microprocessor 59 may be programmed to apply the constant current signal to the stimulating electrodes 12, and to read the voltage signals produced on the sensing electrodes 14 simultaneously while inflating and deflating the balloon 8, in order that the transverse cross-sectional area of the balloon 8 adjacent the respective sensing electrodes 14 may be monitored during inflating and/or deflating of the balloon 8. The computed and monitored values of the transverse cross-sectional area of the balloon 8 adjacent the respective sensing electrodes 14 would then be displayed and continuously updated in the windows 63 on the display screen 24. The volume of the balloon between the extreme-most or selected ones of the sensing electrodes could also be displayed and continuously updated in the window 24 of the display screen 24 during inflating and/or deflating of the balloon 8.

Figure 6:
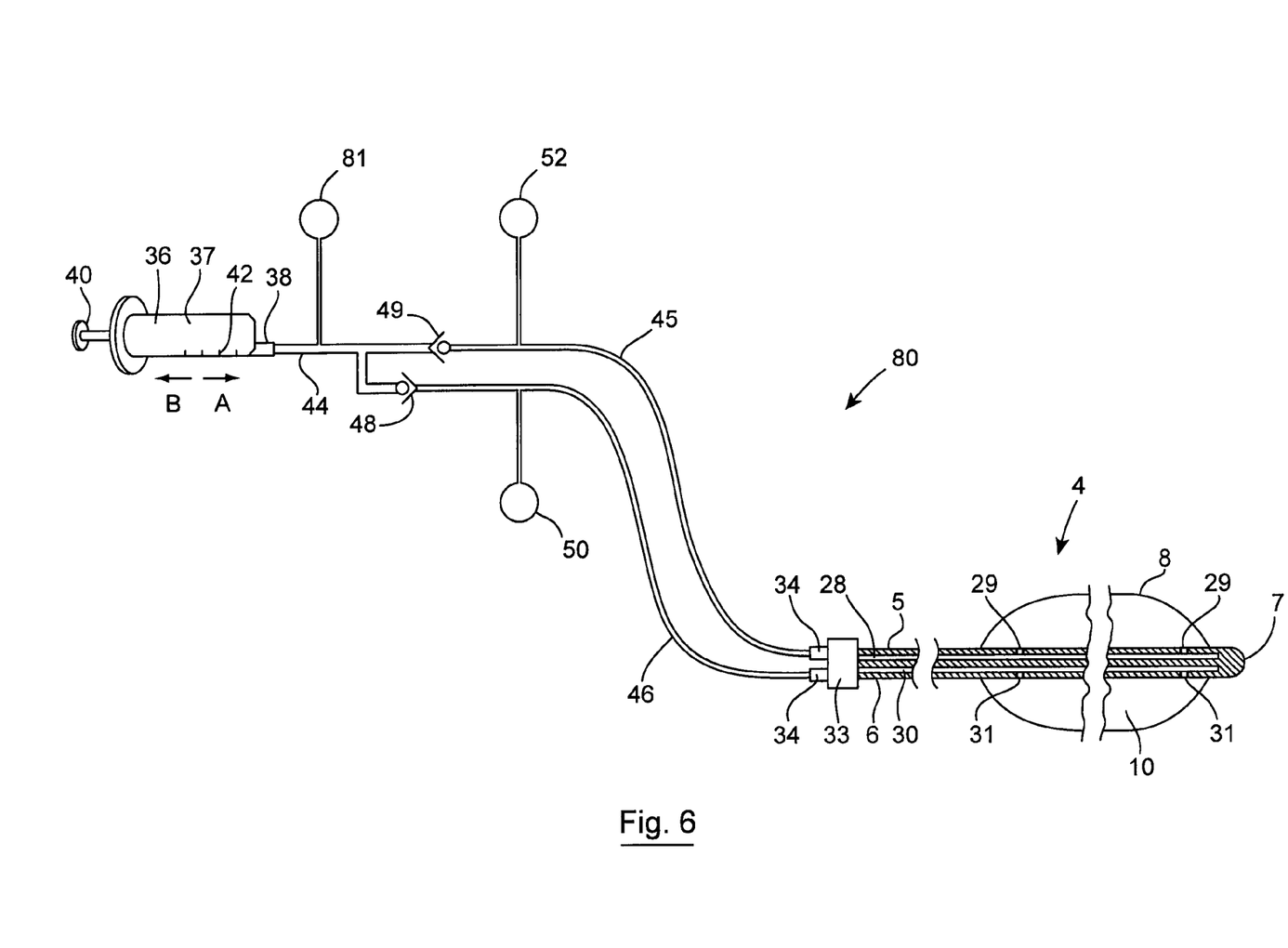
FIG. 6 is a view similar to FIG. 3 of a system according to another embodiment of the invention for inflating the inflatable element of the apparatus of FIG. 1.

Referring now to FIG. 6, there is illustrated a system according to another embodiment of the invention, indicated generally by the reference numeral 80, also for inflating a balloon 8 of a balloon catheter 4 for in turn determining the volume and the transverse cross-sectional area of a vessel or lumen. The system 80 is substantially similar to the system 35 and similar components are identified by the same reference numerals. In the system 80 the first and second secondary pressure sensors 51 and 53 have been omitted, and a third pressure sensor 81, which in this embodiment of the invention is a coarse pressure sensor is coupled to the main fluid line 44 for monitoring the pressure of the liquid inflating medium in the main fluid line 44. In this embodiment of the invention the third pressure sensor 81 replaces the first and second secondary pressure sensors 51 and 53. Additionally, in the system 80 the syringe 36 is horizontally orientated, instead of being vertically orientated. However, in this case the communicating port 38 is offset from the central axis of the syringe barrel 37 towards a sidewall thereof, and the syringe 36 is oriented with the communicating port 38 located at a lower portion of the syringe, so that the top surface of the liquid inflating medium in the syringe barrel 37 is always above the level of the communicating port 38. This thus avoids any danger of air which has been separated from the liquid inflating medium being urged through the communicating port 38 along with the liquid inflating medium as the piston 39 is being urged in the first direction, namely, in the direction of the arrow A for discharging liquid inflating medium from the syringe 36 to the balloon 8.

Otherwise, the system 80 is similar to the system 35, as is its use.

While the apparatus, and the system for inflating the balloon of the balloon catheter, have been described for use in determining the volume and the transverse cross-sectional area of the stomach of a subject, the apparatus and the system may be used for determining the volume and/or the transverse cross-sectional area of a pouch formed in a stomach by bariatric surgery. Indeed, it will be readily apparent to those skilled in the art that the apparatus and the system may be used for determining the volume of any lumen, vessel or organ biological or otherwise, and indeed, the apparatus may be used for determining the volume and/or transverse cross-sectional area of any other vessel be it biological or otherwise.

It will be readily apparent to those skilled in the art that the system according to the invention for inflating an inflatable element may be used for inflating any type of inflatable element be it a balloon of a balloon catheter, or an inflatable element of any other type.

Additionally, it will be appreciated that while the balloon catheter has been described for determining the volume and the transverse cross-sectional area of a vessel, namely, the stomach, the balloon catheter may be used for determining the transverse cross-sectional area of a sphincter, a lumen or any other such lumen or vessel. It is also envisaged that the balloon catheter may be used for determining the transverse cross-sectional area of an occlusion in a lumen or vessel, for example, an occlusion in the oesophagus, caused by a diseased part of the oesophagus. Needless to say, the balloon catheter may be used for determining the transverse cross-sectional area of the colon, the intestine, or an occlusion in the colon or intestine resulting from a diseased portion of the colon or intestine. The balloon catheter may also be used for determining the volume and transverse cross-sectional area of a lumen or vessel in the cardiovascular system, and for determining the transverse cross-sectional area of an occlusion in a vessel of the cardiovascular system, resulting, for example, of a build-up of plaque in the vessel.

The balloon catheter according to the invention may be used for dilating an occlusion in a vessel or lumen, for example, for dilating an occlusion in the oesophagus, intestine or colon resulting from a diseased portion of the oesophagus, intestine or colon, and in which case, the transverse cross-sectional area of the balloon of the balloon catheter adjacent the respective sensing electrodes would be continuously monitored during inflating of the balloon, and the computed values of the transverse cross-sectional area would be displayed on the visual display screen. The pressure of the liquid inflating medium in the balloon would also be monitored, in order to avoid any danger of rupturing the oesophagus, intestine or colon, as the case may be.

The balloon catheter according to the invention may be used for ablating tissue in a vessel or lumen, for example, in the oesophagus, an intestine, colon, and indeed, in the stomach or a pouch of the stomach of a subject, or in a blood vessel, or in any other vessel or lumen. During inflating of the balloon of the balloon catheter, the transverse cross-sectional area of the balloon adjacent the respective sensing electrodes would be continuously monitored, and the values of the transverse cross-sectional area would be displayed on the visual display screen. The pressure of the liquid inflating medium in the balloon would also be monitored, in order to avoid any danger of rupturing of the vessel or lumen in which the balloon is located.

While the system according to the invention has been described as being provided with first main and secondary pressure sensors, and second main and secondary pressure sensors, in certain cases, it is envisaged that only the first and second main pressure sensors may be provided, or alternatively, only the first and second secondary pressure sensors may be provided. Indeed, in certain cases, where it is only desired to monitor the pressure of the inflating medium in the balloon during inflating of the balloon, a single pressure sensor only may be provided in the return line or lumen. Additionally, where it is only desired to monitor the pressure of the liquid inflating medium in the balloon during inflating of the balloon, and to monitor the pressure at which the liquid inflating medium is being delivered by the syringe to the balloon during inflating of the balloon, a first main pressure sensor and a second secondary pressure sensor could be provided only. Needless to say, other appropriate combinations of first and second main and secondary pressure sensors may be provided.

While the pump means has been described as being a syringe, any other suitable pump means for delivering and withdrawing liquid inflating medium to the inflatable element may be provided. Indeed, in certain cases, it is envisaged that separate pump means may be provided for inflating and deflating the inflatable element.

The invention claimed is:

1. A system for inflating an inflatable element with a liquid inflating medium, the system comprising:
    a separating means for separating the liquid inflating medium from a gaseous medium therein,
    a flow line communicating the inflatable element with the separating means,
    a return line communicating the inflatable element with the separating means,
    a pump means selectively operable to alternately deliver the liquid inflating medium from the separating means to the inflatable element and from the inflatable element to the separating means, and
    a valving means communicating the separating means with the flow line and the return line, the valving means being configured to permit flow of the liquid inflating medium from the separating means to the inflatable element through the flow line and to prevent flow of the liquid inflating medium from the separating means to the inflatable element through the return line during inflating of the inflatable element, and to permit flow of the liquid inflating medium from the inflatable element to the separating means through the return line and to prevent flow of the liquid inflating medium from the inflatable element to the separating means through the flow line during deflating of the inflatable element.

2. A system as claimed in claim 1 in which the pump means is operable for sequentially delivering the liquid inflating medium from the separating means to the inflatable element through the flow line, and from the inflatable element to the separating means through the return line until the level of gaseous medium in the liquid inflating medium has been reduced to a desired level.

3. A system as claimed in claim 1 in which the separating means is located intermediate the valving means and the pump means.

4. A system as claimed in claim 1 in which the valving means comprises a first non-return valve located in the return line and a second non-return valve located in the flow line, the first non-return valve being configured for permitting flow of the liquid inflating medium through the return line from the inflatable element to the separating means, and the second non-return valve being configured for permitting flow of the liquid inflating medium through the flow line from the separating means to the inflatable element.

5. A system as claimed in claim 1 in which a pressure sensing means is provided for remotely monitoring the pressure of the liquid inflating medium in the inflatable element.

6. A system as claimed in claim 5 in which the pressure sensing means comprises a first pressure sensing means located in the return line intermediate the separating means and the inflatable element adjacent the valving means.

7. A system as claimed in claim 5 in which the pressure sensing means comprises a second pressure sensing means located in the flow line intermediate the separating means and the inflatable element adjacent the valving means.

8. A system as claimed in claim 1 in which the separating means comprises a reservoir for the liquid inflating medium, the reservoir being configured so that gaseous medium in the liquid inflating medium rises to a top surface of the liquid inflating medium in the reservoir for separating the liquid inflating medium from the gaseous medium.

9. A system as claimed in claim 8 in which the reservoir comprises an elongated barrel of a syringe, the barrel having a communicating port for communicating the barrel with the flow and return lines, and the pump means comprises a piston slideable axially within the barrel of the syringe in a first direction for drawing the liquid inflating medium into the barrel, and in an opposite second direction for discharging the liquid inflating medium from the barrel.

10. A system as claimed in claim 9 in which the syringe is configured so that the gaseous medium in the liquid inflating medium rises through the liquid inflating medium in the barrel to a liquid inflating medium/piston interface so that the gaseous medium is trapped between the piston and liquid inflating medium.

11. A system as claimed in claim 1 in which the inflatable element is located on an elongated catheter extending between a proximal end and a distal end, a flow lumen and a return lumen extending from the proximal end of the catheter to the inflatable element and communicating with the inflatable element, the flow lumen forming a part of the flow line, and the return lumen forming a part of the return line.

12. A system as claimed in claim 11 in which the catheter extends through the inflatable element, and the inflatable element defines with the catheter an annular hollow interior region extending around the catheter.

13. A system as claimed in claim 12 in which at least one stimulating electrode is located within the inflatable element on one of the catheter and an inner surface of the inflatable element, and at least one sensing electrode is located within the inflatable element on one of the catheter and the inner surface of the inflatable element axially spaced apart from the at least one stimulating electrode, and a communicating means is provided for facilitating applying a stimulating signal to the at least one stimulating electrode and reading a signal produced on the at least one sensing electrode in response to the stimulating signal applied to the at least one stimulating electrode when the inflatable element is inflated with an electrically conductive inflating medium.

14. Apparatus for determining one of a volume and a transverse cross-sectional area of one of a lumen and a vessel, the apparatus comprising
a balloon catheter comprising
an elongated catheter extending between a proximal end and a distal end,
an inflatable element located on the catheter with the catheter extending through the inflatable element, the inflatable element defining with the catheter an annular hollow interior region extending around the catheter,
a flow lumen extending through the catheter from the proximal end thereof to the inflatable element communicating with the inflatable element,
a return lumen extending through the catheter from the proximal end thereof to the inflatable element communicating with the inflatable element,
at least one stimulating electrode located within the hollow interior region of the inflatable element on one of the catheter and an inner surface of the inflatable element,
at least one sensing electrode located within the hollow interior region of the inflatable element on one of the catheter and the inner surface of the inflatable element axially spaced apart from the at least one stimulating electrode,
a communicating means for facilitating applying a stimulating signal to the at least one stimulating electrode and reading a signal produced on the at least one sensing electrode in response to the stimulating signal applied to the at least one stimulating electrode when the inflatable element is inflated with an electrically conductive inflating medium,
a separating means for storing an electrically conductive liquid inflating medium for inflating the inflatable element, and for separating the liquid inflating medium from a gaseous medium therein,
a pump means selectively operable to alternately deliver the liquid inflating medium from the separating means to the inflatable element and from the inflatable element to the separating means,
a valving means communicating the separating means with the flow lumen and the return lumen, the valving means being configured to permit flow of the liquid inflating medium from the separating means to the inflatable element through the flow lumen and to prevent flow of the liquid inflating medium from the separating means to the inflatable element through the return lumen during inflating of the inflatable element, and to permit flow of the liquid inflating medium from the inflatable element to the separating means through the return lumen and to prevent flow of the liquid inflating medium from the inflatable element to the separating means through the flow lumen during deflating of the inflatable element,
a signal generator in communication with the at least one stimulating electrode through the communicating means for applying a stimulating signal to the at least one stimulating electrode, and
a signal processing means in communication with the at least one sensing electrode through the communicating means for reading a signal produced on the at least one sensing electrode in response to the stimulating signal applied to the at least one stimulating electrode when the inflatable element is inflated with the electrically conductive liquid inflating medium, the signal processing means being adapted to determine one of the volume and the transverse cross-sectional area of the inflated inflatable element.

15. Apparatus as claimed in claim 14 in which two axially spaced apart stimulating electrodes are provided within the inflatable element, and a plurality of axially spaced apart sensing electrodes are located between and spaced apart from the stimulating electrodes.

16. Apparatus as claimed in claim 14 in which the communicating means comprises an electrically conducting means extending from the proximal end of the catheter to the respective stimulating and sensing electrodes, and a communicating lumen extends through the catheter from the proximal end thereof to the inflatable element for accommodating the electrically conducting means from the proximal end of the catheter to the respective stimulating and sensing electrodes.

17. A method for inflating an inflatable element with a liquid inflating medium, the method comprising:
providing a separating means for separating the liquid inflating medium from a gaseous medium therein,
providing a flow line communicating the inflatable element with the separating means,
providing a return line communicating the inflatable element with the separating means,
providing a pump means selectively operable to alternately deliver the liquid inflating medium from the separating means to the inflatable element and from the inflatable element to the separating means,
providing a valving means communicating the separating means with the flow line and the return line,
configuring the valving means to permit flow of the liquid inflating medium from the separating means to the inflatable element through the flow line and to prevent flow of the liquid inflating medium from the separating means to the inflatable element through the return line during inflating of the inflatable element, and to permit flow of the liquid inflating medium from the inflatable element to the separating means through the return line and to prevent flow of the liquid inflating medium from the inflatable element to the separating means through the flow line during deflating of the inflatable element,
operating the pump means to inflate the inflatable element by delivering the liquid inflating medium from the separating means to the inflatable element through the flow line and to simultaneously displace a gaseous medium in the flow line and the inflatable element to the return line from the inflatable element,
operating the pump means to deflate the inflatable element by delivering the liquid inflating medium from the inflatable element through the return line along with the gaseous medium to the separating means,
separating the liquid inflating medium from the gaseous medium in the separating means, and
operating the pump means to reinflate the inflatable element by delivering the separated liquid inflating medium from the separating means through the flow line to the inflatable element.

18. A method as claimed in claim 17 in which the method further comprises sequentially operating the pump means to deflate the inflatable element by delivering the liquid inflating medium from the inflatable element through the return line along with any remaining gaseous medium to the separating means, separating the liquid inflating medium from the gaseous medium in the separating means, and operating the pump means to reinflate the inflatable element by delivering the separated liquid inflating medium from the separating means through the flow line to the inflatable element until the level of the gaseous medium in the liquid inflating medium has been reduced to a desired level.

19. A method for inflating an inflatable element of a balloon catheter with a liquid inflating medium, the balloon catheter comprising an elongated catheter extending from a proximal end to a distal end, an inflatable element located on the catheter, a flow lumen extending through the catheter from the proximal end thereof to the inflatable element communicating with the inflatable element for accommodating the liquid inflating medium during inflating of the inflatable element, a return lumen extending through the catheter from the proximal end thereof to the inflatable element communicating with the inflatable element for accommodating the liquid inflating medium during deflating of the inflatable element, the method comprising:
- providing a separating means for storing a liquid inflating medium for inflating the inflatable element, and for separating the liquid inflating medium from a gaseous medium therein,
- providing a pump means selectively operable to alternately deliver the liquid inflating medium from the separating means to the inflatable element and from the inflatable element to the separating means,
- providing a valving means communicating the separating means with the flow lumen and the return lumen,
- configuring the valving means to permit flow of the liquid inflating medium from the separating means to the inflatable element through the flow lumen and to prevent flow of the liquid inflating medium from the separating means to the inflatable element through the return lumen during inflating of the inflatable element, and to permit flow of the liquid inflating medium from the inflatable element to the separating means through the return lumen and to prevent flow of the liquid inflating medium from the inflatable element to the separating means through the flow lumen during deflating of the inflatable element,
- operating the pump means to inflate the inflatable element by delivering the liquid inflating medium from the separating means to the inflatable element through the flow lumen and to simultaneously displace a gaseous medium in the flow lumen and the inflatable element to the return lumen,
- operating the pump means to deflate the inflatable element by delivering the liquid inflating medium from the inflatable element through the return lumen along with the gaseous medium to the separating means,
- separating the liquid inflating medium from the gaseous medium in the separating means, and
- operating the pump means to reinflate the inflatable element by delivering the separated liquid inflating medium from the separating means through the flow lumen to the inflatable element.

20. A method as claimed in claim 19 in which the method further comprises sequentially operating the pump means to deflate the inflatable element by delivering the liquid inflating medium from the inflatable element through the return lumen along with any remaining gaseous medium to the separating means, separating the liquid inflating medium from the gaseous medium in the separating means, and operating the pump means to reinflate the inflatable element by delivering the separated liquid inflating medium from the separating means through the flow lumen to the inflatable element until the level of the gaseous medium in the liquid inflating medium is at a desired level.

21. A balloon catheter comprising:
- an elongated catheter extending between a proximal end and a distal end,
- an inflatable element located on the catheter with the catheter extending through the inflatable element, and the inflatable element defining with the catheter an annular hollow interior region extending around the catheter,
- a flow lumen extending from the proximal end of the catheter to the inflatable element and communicating with the inflatable element,
- a return lumen extending from the proximal end of the catheter to the inflatable element and communicating with the inflatable element,
- at least one stimulating electrode located within the inflatable element on one of the catheter and an inner surface of the inflatable element,
- at least one sensing electrode located within the inflatable element on one of the catheter and the inner surface of the inflatable element axially spaced apart from the at least one stimulating electrode,
- a communicating means for facilitating applying a stimulating signal to the at least one stimulating electrode and reading a signal produced on the at least one sensing electrode in response to the stimulating signal applied to the at least one stimulating electrode when the inflatable element is inflated with an electrically conductive inflating medium,
- a system for inflating the inflatable element with an electrically conductive liquid inflating medium, the system comprising:
  - a separating means for separating the liquid inflating medium from a gaseous medium therein,
  - a flow line communicating the inflatable element with the separating means through the flow lumen,
  - a return line communicating the inflatable element with the separating means through the return lumen,
  - a pump means selectively operable to alternately deliver the liquid inflating medium from the separating means to the inflatable element and from the inflatable element to the separating means, and
  - a valving means communicating the separating means with the flow line and the return line, the valving means being configured to permit flow of the liquid inflating medium from the separating means to the inflatable element through the flow line and the flow lumen and to prevent flow of the liquid inflating medium from the separating means to the inflatable element through the return line and the return lumen during inflating of the inflatable element, and to permit flow of the liquid inflating medium from the inflatable element to the separating means through the return line and the return lumen and to prevent flow of the liquid inflating medium from the inflatable element to the separating means through the flow line and the flow lumen during deflating of the inflatable element.

\* \* \* \* \*